US006566336B1

(12) United States Patent
Sugiyama et al.

(10) Patent No.: US 6,566,336 B1
(45) Date of Patent: May 20, 2003

(54) COMPOUNDS ALKYLATING SPECIFIC BASE SEQUENCE OF DNA AND METHOD FOR SYNTHESIZING THE SAME

(75) Inventors: Hiroshi Sugiyama, Tokyo (JP); Zhi Fu Tao, Tokyo (JP); Isao Saito, Kyoto (JP)

(73) Assignee: Japan Science and Technology Corporation (JP)

( * ) Notice: Subject to any disclaimer, the term of this patent is extended or adjusted under 35 U.S.C. 154(b) by 0 days.

(21) Appl. No.: 09/486,336

(22) PCT Filed: Mar. 12, 1999

(86) PCT No.: PCT/JP99/01228

§ 371 (c)(1),
(2), (4) Date: May 30, 2000

(87) PCT Pub. No.: WO00/15641

PCT Pub. Date: Mar. 23, 2000

(30) Foreign Application Priority Data

Sep. 14, 1998 (JP) ............................................. 10-260710

(51) Int. Cl.[7] ............................................... C07K 14/00
(52) U.S. Cl. ........................ 514/18; 530/330; 530/331; 548/311.1
(58) Field of Search ........................ 514/18, 397, 398; 530/330, 331; 548/311.1, 312.7, 315.1, 328.5

(56) References Cited

PUBLICATIONS

Gomi et al., Japanese Journal of Cancer Research (1992) 83:113–120.*
Lehninger, Principles of Biochemistry, 2d Ed., Worth Publishers, NY (1993) p. 974.*
Fujiwara et al., "Sequence Selective DNA Alkylation by Duocarmycin Derivatives Using Molecular Recognition of Pyrrole–imidazole Polyamide", Nucleic Acids Symposium Series, 1998, No. 39, pp. 101–102.
Sugiyama et al., "Distamycin A Modulates the Sequence Specificity of DNA Alkylation by Duocarmycin A", Proceedings of the National Academy of Science of the United States of America, 1996, vol. 93, No. 25, pp. 14405–14410.
Isomura et al., "Efficient Guanine Alkylation Through Cooperative Heterodimeric Formation of Duocarmycin A and Distamycin", Nucliec Acids Symposium Series, 1995, No. 34, pp. 47–48.

Okamoto et al., "Differential Effect of Duocarmycin A and Its novel Derivative DU–86 on DNA Strand Breaks in HeLa S3 Cells", Japanese Journal of Cancer Research, 1994, vol. 85, No. 12, p. 1304–1311.
Yamamoto et al., "Concerted DNA Recognition and Novel Site–Specific Alkylation by Duocarmycin A with Distamicin A", Biochemistry, 1993, vol. 32, No. 4, pp. 1059–1066.
Sugiyama et al., "A Novel Guanine N3 Alkylation by Antitumor Antibiotic Duocarmycin A", Tetrahedron Letters, 1993, vol. 34, No. 13, p. 2179–2182.
Asai et al., A Novel Property of Duocarmycin and Its Analogues for Covalent Reaction with DNA, 1994, vol. 116, No. 10, p. 4171–4177.
De Clairac et al., "NMR Characterization of Hairpin Polyamide Complexes with the Minor Groove of DNA", 1997, Journal of the American Chemical Society, vol. 119, No. 34, p. 7909–7916.
Dickinson, et al., Proc. Natl. Acad. Sci. USA, vol. 95, pp. 12890–12895, Oct. 1998, Biochemistry.
Gottesfeld et al., Nature vol. 387, pp. 202–205, May 8, 1997.
Tao, et al., J. Am. Chem. Soc. 1999, vol. 121, pp. 4961–4967.

\* cited by examiner

Primary Examiner—Karen Cochrane Carlson
(74) Attorney, Agent, or Firm—Peter F. Corless; Christine C. O'Day; Edwards & Angell, LLP

(57) ABSTRACT

The invention provides a compound recognizing the minor group of hydrogen bonds between base pairs and being capable of forming a covalent bond with bases. The inventive compound can recognize a specific nucleotide sequence and can strongly bind to adjacent bases via covalent bonding, to regulate the expression of a DNA with the nucleotide sequence. The invention provides a DNA alkylating agent comprising a compound represented by the general formula I:

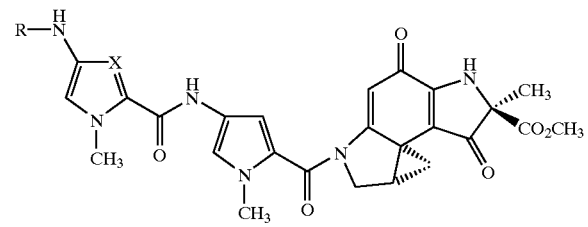

wherein R represents a lower amyl group or a polyamide group; and X represents nitrogen or CH.

9 Claims, 8 Drawing Sheets

IPDu: X=N
PPDu: X=CH

SEQUENCE LISTING

<160> NUMBER OF SEQ ID NOS: 3

<210> SEQ ID NO 1
<211> LENGTH: 450
<212> TYPE: DNA
<213> ORGANISM: pUC 18

<400> SEQUENCE: 1

-continued

```
agaatcaggg gataacgcag gaaagaacat gtgagcaaaa ggccagcaaa aggccaggaa      60
ccgtaaaaag gccgcgttgc tggcgttttt ccataggctc cgcccccctg acgagcatca     120
ccgtaaaaag gccgcgttgc tggcgttttt ccataggctc cgcccccctg acgagcatca     180
gtttccccct ggaagctccc tcgtgcgctc tcctgttccg accctgccgc ttaccggata     240
cctgtccgcc tttctccctt cgggaagcgt ggcgctttct caatgctcac gctgtaggta     300
tctcagttcg tgtaggtcg ttcgctccaa gctgggctgt gtgcacgaac ccccgttca      360 gcccgaccgc tgcgccttat ccgtaacta tcgtcttgag tccaacccgg taagacacga     420
cttatcgcca ctggcagcag ccactggtaa                                     450
```

<210> SEQ ID NO 2
<211> LENGTH: 450
<212> TYPE: DNA
<213> ORGANISM: pUC 18

<400> SEQUENCE: 2

```
tgtaaaacga cggccagtgc caagcttgca tgcctgcagg tcgactctag aggatccccg      60
ggtaccgagc tcgaattcgt aatcatggtc atagctgttt cctgtgtgaa attgttatcc     120
gctcacaatt ccacacaaca tacgagccgg aagcataaag tgtaaagcct ggggtgccta     180
atgagtgagc taactcacat taattgcgtt gcgctcactg cccgctttcc agtcgggaaa     240
cctgtcgtgc cagctgcatt aatgaatcgg ccaacgcgcg gggagaggcg gtttgcgtat     300
tgggcgctct tccgcttcct cgctcactga ctcgctgcgc tcggtcgttc ggctgcggcg     360
agcggtatca gctcactcaa aggcggtaat acggttatcc acagaatcag ggataacgc      420 aggaaagaac atgtgagcaa aaggccagca                                     450
```

<210> SEQ ID NO 3
<211> LENGTH: 426
<212> TYPE: DNA
<213> ORGANISM: pUC 18

<400> SEQUENCE: 3

```
ggtcacagct tgtctgtaag cggatgccgg gagcagacaa gcccgtcagg gcgcgtcagc      60
gggtgttggc gggtgtcggg gctggcttaa ctatgcggca tcagagcaga ttgtactgag     120
agtgcaccat atgcggtgtg aaataccgca cagatgcgta aggagaaaat accgcatcag     180
gcgccattcg ccattcaggc tgcgcaactg ttgggaaggg cgatcggtgc gggcctcttc     240
gctattacgc cagctggcga aaggggatg tgctgcaagg cgattaagtt gggtaacgcc      300
agggttttcc cagtcacgac gttgtaaaac gacggccagt gccaagcttg catgcctgca     360
ggtcgactct agaggatccc cgggtaccga gctcgaattc gtaatcatgg tcatagctgt     420
ttcctg                                                               426
```

US 6,566,336 B1

COMPOUNDS ALKYLATING SPECIFIC BASE SEQUENCE OF DNA AND METHOD FOR SYNTHESIZING THE SAME

This application is a national stage application of PCT/JP99/01228, filed Mar. 12, 1999, which claims priority to Japanese application JP 10-260710/1998, filed Sep. 14, 1998.

TECHNICAL FIELD OF THE INVENTION

The present invention relates to a compound capable of alkylating a gene, an alkylating agent using the compound, a method for controlling the expression of the gene by using the alkylating agent, and a pharmaceutical composition containing the compound.

BACKGROUND ART

The rapid progress in molecular biology sequentially elucidates that the etiology of various diseases including cancer lies in DNA mutation. Furthermore, it is believed that the human genome project will complete the determination of the whole nucleotide sequence of human DNA within two or three years. Accordingly, it is increasingly expected the development of therapeutic methods of these diseases based on molecular-level findings. However, the practical application of these approaches is barred by such a serious barrier that not any general technology has been established for regulating gene expression extracellularly. In recent years, molecules binding to specific nucleotide sequences have been designed on the basis Of the recognition of DNA molecules by antibiotics such as distamycin. Hence, it can be said that gene expression is now possibly under regulation.

X-ray crystallography and NMR have elucidated that crescent-shape antibiotics such as distamycin and netropsin bind to the minor groove of DNA via hydrogen bonds between adenine (sometimes abbreviated as A hereinbelow) and thymine (sometimes abbreviated as T hereinbelow) in a DNA sequence with abundant A-T base pairs. Various molecules have been synthetically produced by utilizing the recognition. It has been speculated so far that the antibiotics will acquire an ability to recognize guanine-cytosine base pairs (G-C; guanine is sometimes abbreviated as G hereinbelow; cytosine is sometimes abbreviated as C hereinbelow), when the pyrrole ring is modified into imidazole [M. L. Kopla, C. Yoon, D. Goodsell, P. Pjura, R. E. Dickerson, Proc. Natl. Acad. Sci. USA, 82, 1376 (1985); J. W. Lown, K. Krowickl, U. G. Bhat, A. Skorobogaty, B. Ward, J. C. Dabrowiak, Biochemistry, 25, 7408 (1986)]. Practically, it never has been so simple. Hence, numerous intriguing experimental results have been reported.

Wemmer et al. examined distamycin bound DNA in detail by NMR. Consequently, they verified that two disks of distamycin can be stacked in the DNA miner group, where it has been believed that only one disk thereof can be placed [J. G. Pelton, D. E. Wemmer, Proc. Natl. Acad. Sci. USA, 86, 5723 (1989)]. Focusing attention to the binding mode by which the intriguing results hitherto can be explained, Dervan et al. demonstrated that the nucleotide sequence of a double-stranded DNA can be recognized by a polyamide comprising a pair of methylpyrrole (sometimes abbreviated as Py hereinbelow) and methylimidazole (sometimes abbreviated as Im hereinbelow) in an anti-parallel orientation.

More specifically, they introduced a general rule that Py-Im recognizes C-G base pair; Im-Py recognizes G-C base pair; and Py-Py recognizes A-T or T-A base pair [S. White, E. E. Baird, P. B. Dervan, Chemistry & Biology, 4, 569 (1997)]. Various polyamides in hair-pin structures or cyclic polyamides have been synthetically produced, so as to introduce a covalent bond in such pairs to prevent the entropy loss during binding, thereby generating stronger binding and higher recognition potency. It is also elucidated that a hair-pin structure with a γ-linker represented by the formula —NHCH$_2$CH$_2$CH$_2$CO— particularly exerts excellent binding and recognition potencies. The structure of a complex thereof with DNA is also determined [R. P. L. de Clairac, B. H. Geierstanger, M. Marksich, P. B. Dervan, D. E. Wemmer, J. Am. Chem. Soc., 119, 7909 (1997)].

Hair-pin polyamides just composed of pyrrole and imidazole can recognize base pairs up to 7 [J. M. Turner, E. F. Baird, P. B. Dervan, ibid., 119, 7636 (1997)]. When a β-alanine pair recognizing A-T sequence is introduced into a homo-dimer system, 11 base pairs can be recognized [S. E. Swalley, E. E. Baird, D. B. Dervan, Chem. Eur. J., 3, 1600 (1997)].

Furthermore, Dervan, Gottesfeld et al. designed a polyamide capable of binding to the fourth finger in the recognition sequence of one of Zn finger proteins, namely TFIIIA, in a manner antagonistic against a minor group of sequences to potentially bind to the fourth finger and then revealed that the expression of 5S RNA could be regulated selectively at in vitro experiments [J. M. Gottesfeld, L. Neely, J. W. Trauger, E. E. Baird, P. B. Dervan, Nature, 387, 202 (1997)]. Additionally, they simultaneously demonstrated that the polyamide permeated into nuclei at in vitro experiments.

Recent attention has been drawn toward oligonucleotides and peptide nucleic acids (PNA), as tools for gene regulation. However, these molecules suffered lower cell permeability. Taking account of significant cell permeability of methylpyrrole-methylimidazole polyamides, these molecules are promising compounds as a molecule regulating gene expression, a powerful tool in molecular biology, and a human medicine.

Conventional polyamides of Py-Im series never bind to gene via a covalent bond but only recognize in the minor groove hydrogen bonds between base pairs.

DISCLOSURE OF THE INVENTION

The present invention provides a compound recognizing the minor group of hydrogen bonds between base pairs and being capable of forming a covalent bond with bases. The inventive compound can recognize a specific nucleotide sequence and can strongly bind to adjacent bases via covalent bonding, to regulate the expression of a DNA with the nucleotide sequence.

The invention relates to a compound represented by the general formula I:

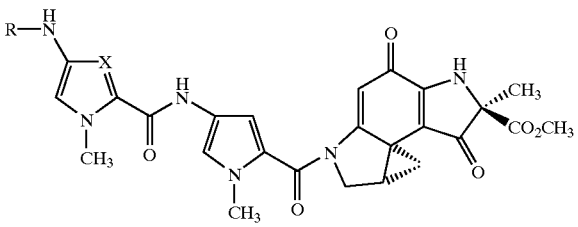

wherein
R represents a lower amyl group or a polyamide group; and X represents nitrogen or CH;
wherein R represents a lower alkyl group or a polyamide group;

and X represents nitrogen or CH.

The invention relates to an alkylating agent of gene, comprising a compound represented by the general formula I. More specifically, the inventive alkylating agent recognizes a specific nucleotide sequence in a gene, such as W-W-V wherein V represents A or G; and W represents A or T or U (abbreviation of uracil), or G-W-V wherein V represents A or G; and W represents A or T or U, thereby selectively alkylating the sequence.

Furthermore, the invention relates to a method for regulating the expression of a gene region including a specific nucleotide sequence, by using the alkylating agent.

Still furthermore, the invention relates to a pharmaceutical composition for the treatment and prophylaxis of various gene-inducible diseases, the composition containing a compound represented by the general formula I.

BEST MODE FOR CARRYING OUT THE INVENTION

The lower amyl group as R in the general formula I of the invention includes a lower acyl group with 1 to 12 carbon atoms (including the carbon atoms in the group U), preferably 2 to 6 carbon atoms, for example acetyl group, N-propionyl group, isopropionyl group and N-butanoyl group. Preferable is a lower acyl group of a small configuration.

Additionally, the polyamide group as R includes polyamides comprising aminocarboxylic acids, such as N-methyl-4-amino-2-carboxypyrrole (abbreviated as HO-Py-H), N-methyl-4-amino-2-carboxyimidazole (abbreviated as HO-Im-H), and 4-aminobutyric acid (abbreviated as HO-γ-H) (for γ-linkers). The nitrogen-hydrogen bonding sites in the amide groups of these polyamides recognize gene sequences; in other words, generally, Py-Im recognizes C-G base pair; Im-Py recognizes G-C pair; and Py-Py recognizes A-T pair or T-A pair. Depending on the nucleotide sequence to be recognized, a polyamide can be designed.

The number of amide groups in the polyamide group as R is 5 to 7, preferably 3 at most, for one base of a base pair in a gene; the number may be larger, but even in that case, the affinity with nucleotide sequences cannot any more be enhanced. Preferable polyamide groups include N-methyl-4-acetylamino-imidazole-2-carbonyl group.

The γ-aminobutyric acid moiety in the polyamide group as R functions as γ-linker, where the polyamide chain curves in a hair-pin shape, to recognize a base pair in the nucleotide sequence of a double-stranded DNA.

In accordance with the invention, the polyamide group as R in the general formula I is preferably a polyamide group represented by the following formula:

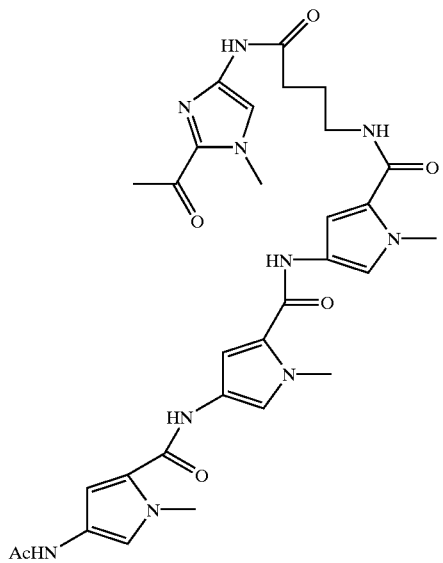

In accordance with the invention, the alkylating moiety in a compound represented by the general formula I serves for alkylation with the same mechanism as the alkylation mechanism of duocarmycin A.

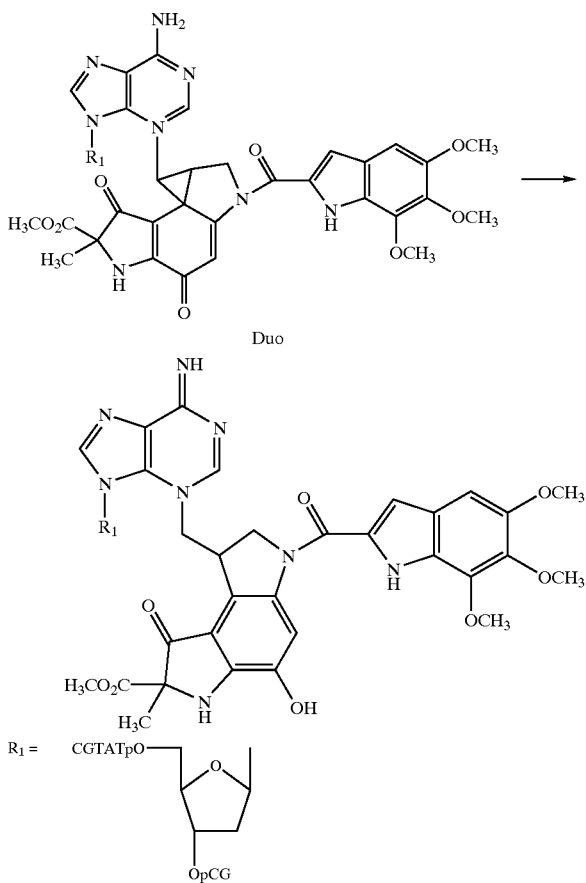

However, the alkylation with duocarmycin A occurs only at the purine ring of adenine (A), while the alkylation with the inventive compound occurs in a different manner, namely both at the purine ring of adenine (A) and at the purine ring of guanine (G).

The moiety Py-Py- following the amide bond of the inventive compound functions to recognize the nucleotide sequence W-W (wherein W represents A or T or U) in a gene; and the moiety Im-Py- functions to recognize the nucleotide sequence G-W (wherein W represents A or T or U) in a gene. Thus, the inventive compound can recognize the following nucleotide sequence represented by the formula II or III:

wherein V represents A or G and W represents A or T or U, thereby covalently binding to the gene at the base V (A or G).

Nevertheless, the inventive alkylating agent is not limited to these nucleotide sequences. As described above, a target nucleotide sequence can be designed, depending on the need.

By further elongating the polyamide bond at the R moiety, a recognizable nucleotide sequence can additionally be elongated.

Figure 1:
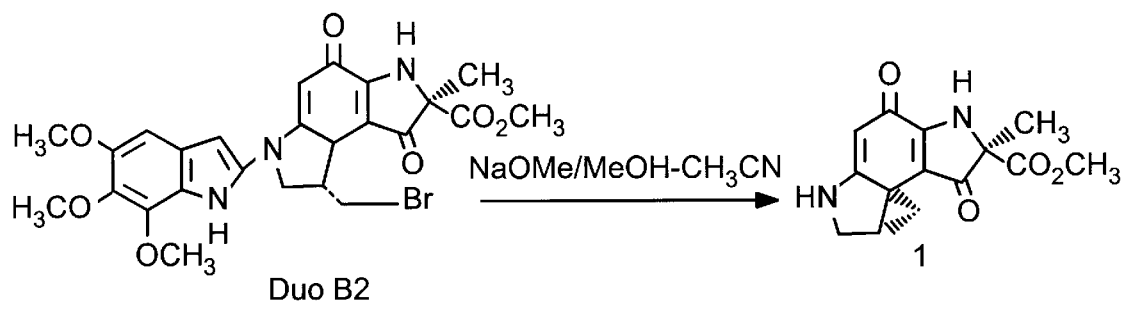
FIG. 1 exemplifies a method for producing the inventive compound.
Figure 1:
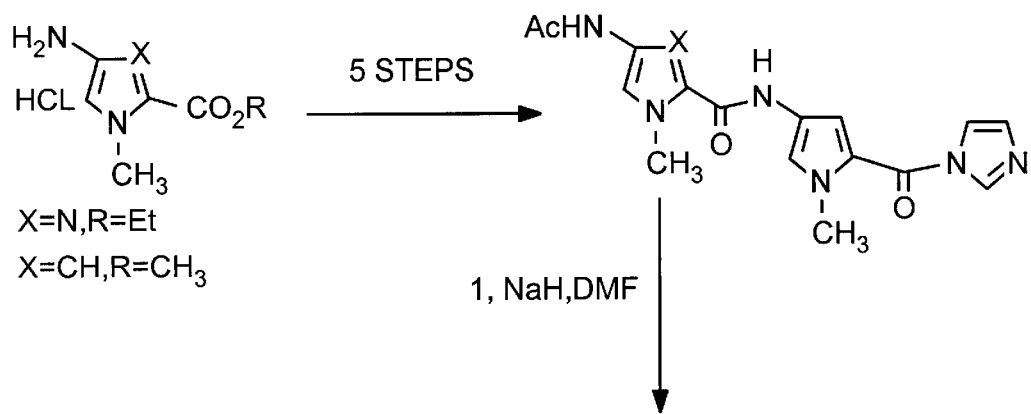
Figure 1:
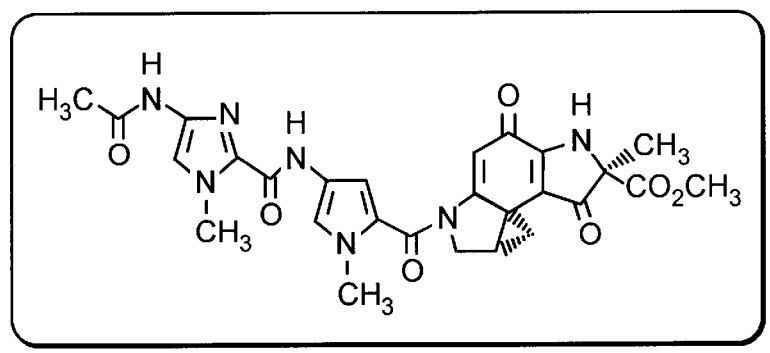

The inventive compound represented by the general formula I can be produced by a method depicted in FIG. 1 (FIG. 1 depicts the compound with an acetyl group as R). The alkylating moiety of the inventive compound can be produced by the method in FIG. 1 from a raw material duocarmycin B2 (abbreviated as Duo B2). Then, the inventive compound can be produced by amidating the resulting alkylating moiety by using an alternatively produced pyrrolecarboxylic acid derivative. More specific production examples are described in the following examples.

Figure 2:
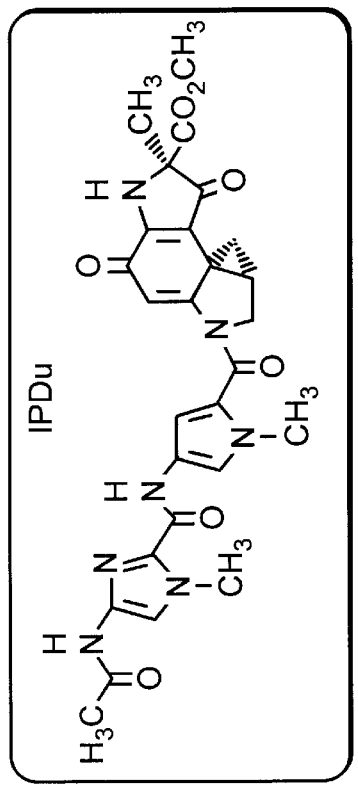
FIG. 2 shows reactivity for the alkylation with IPDu-Dist, wherein a sequence mismatched with IPDu-Dist exerts low reactivity.

One inventive compound wherein X is nitrogen and R is acetyl group (referred to as IPDu hereinafter) was allowed to recognize various 8-bp oligonucleotides. The results are shown in FIG. 2. At the test in FIG. 2, the inventive compound IPDU and distamycin used are expressed with symbols -●-○-△ and +) -◇-○-○-○, respectively (in the figure, the symbol ○ is expressed in gray). Covalent bonding is formed between the site expressed with △ in the inventive compound and the gene.

As described insofar, IPDu recognizes a nucleotide sequence G-W-V (wherein V represents A or G and W represents A or T or U), so among 4 oligonucleotides in FIG. 2, IPDu recognizes oligonucleotides with G-T-G (two oligonucleotides on the left of FIG. 2) and an oligonucleotide with G-A-G (one oligonucleotide on the lower right of FIG. 2) to efficiently form a covalent bond, while IPDu is mismatched with an oligonucleotide with a nucleotide sequence A-T-G different from the recognition sequences above (on the upper right of FIG. 2) and therefore recognizes the oligonucleotide just slowly at a rate of about 8% even after 46 hours. As has been described above, the inventive compound can thoroughly recognize these sequences.

Figure 6:
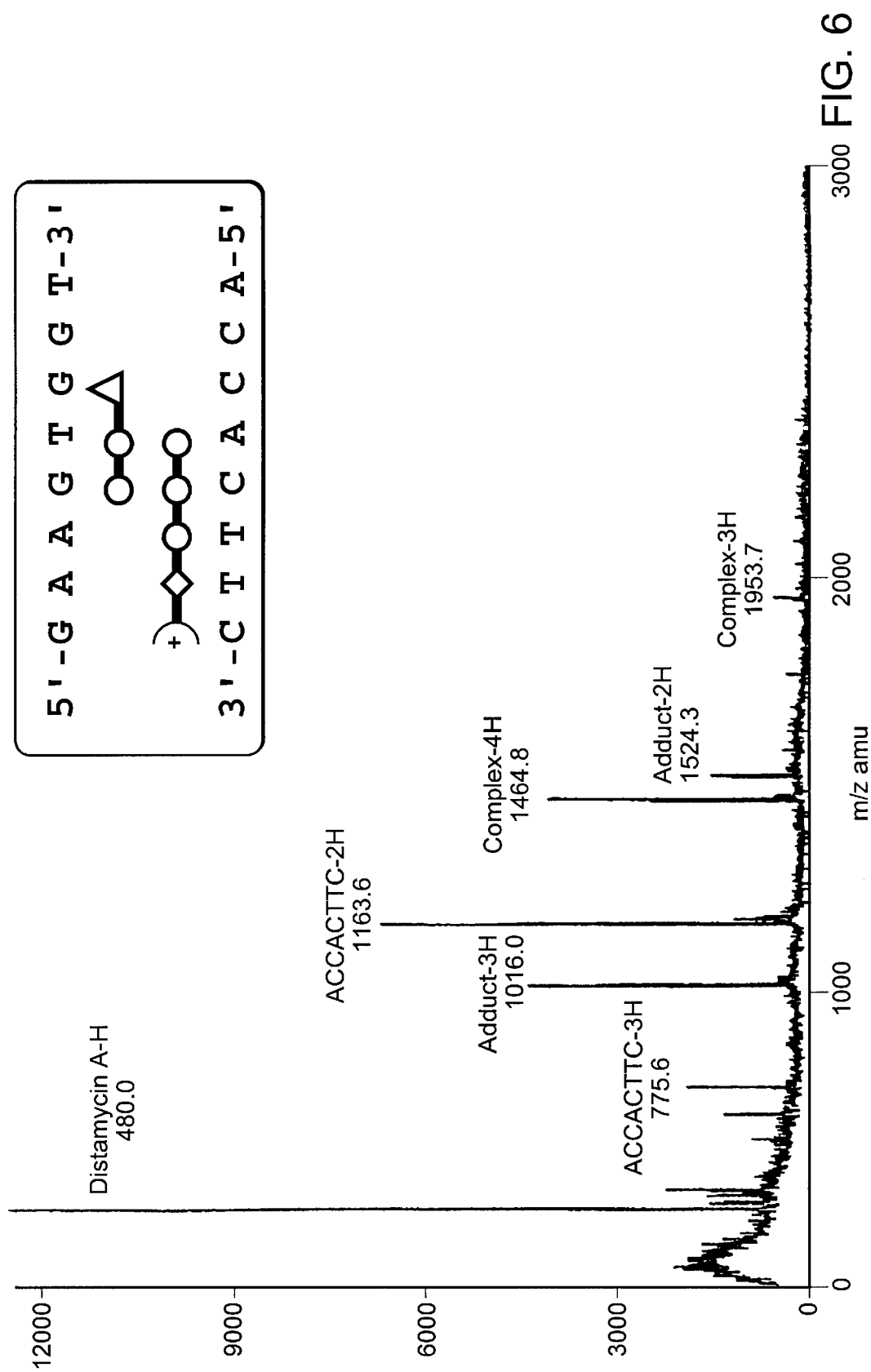
FIG. 6 depicts a spectral chart of an IPDu-Dist-8-mer complex by electro-spray Mass.
Figure 7A:
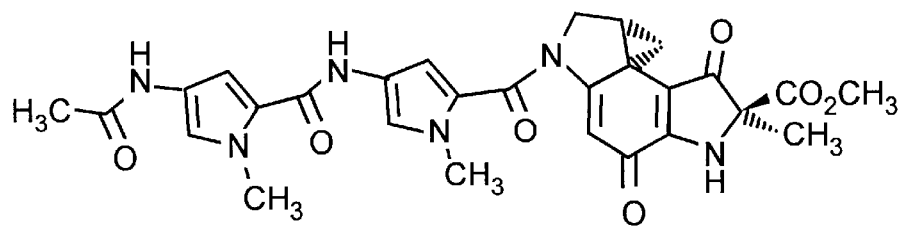
FIG. 7 exemplifies preferable compounds in accordance with the invention.
Figure 7A:
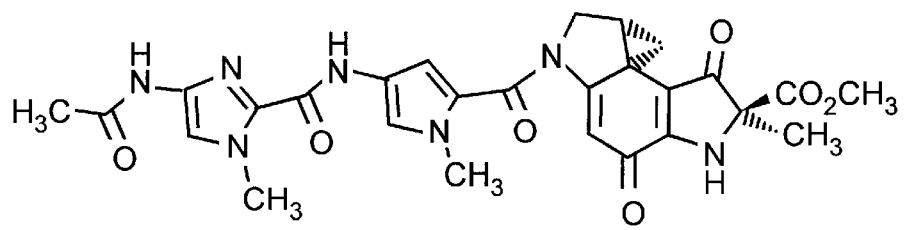
Figure 7B:
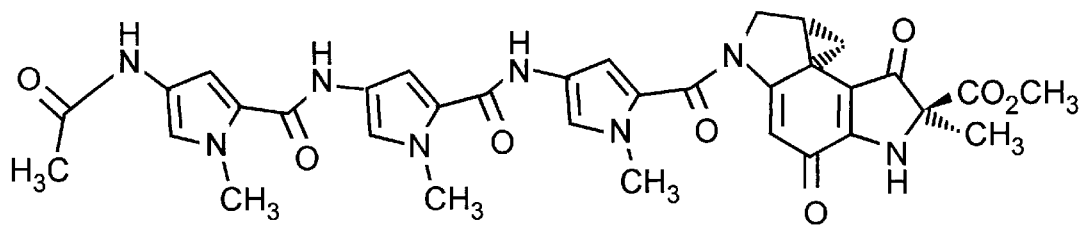
Figure 7B:
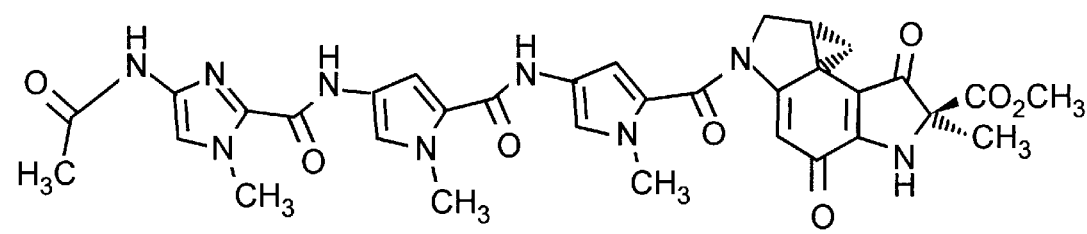
Figure 7B:
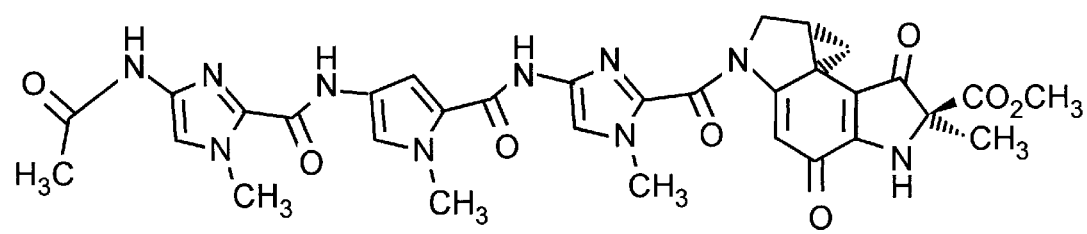
Figure 7C:
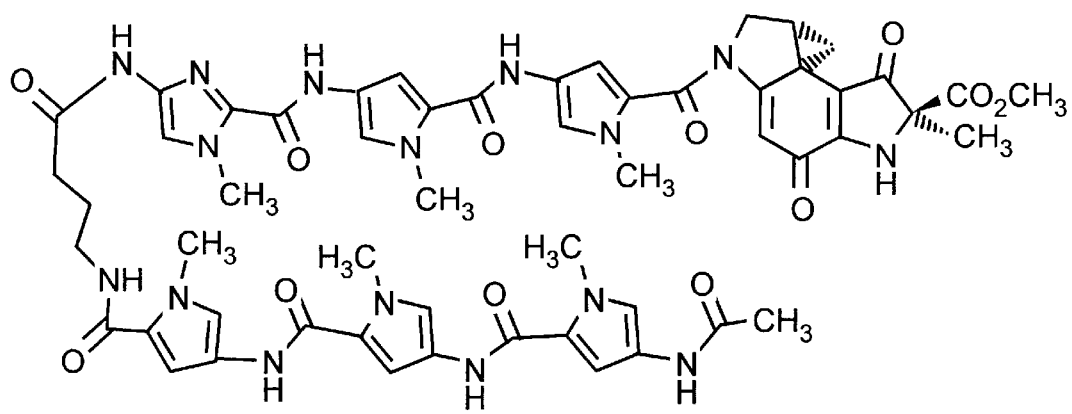
Figure 7C:
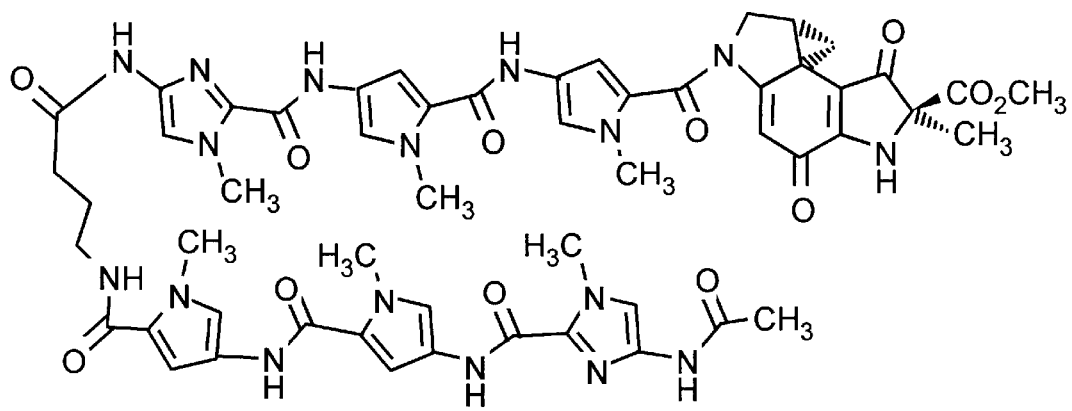

The oligonucleotide on the lower left of FIG. 2 is most highly matched. The oligonucleotide was analyzed by electro-spray MASS. The results are shown in FIG. 6. The MASS spectrum chart indicates that the inventive compound is covalently bound to DNA.

Figure 3:
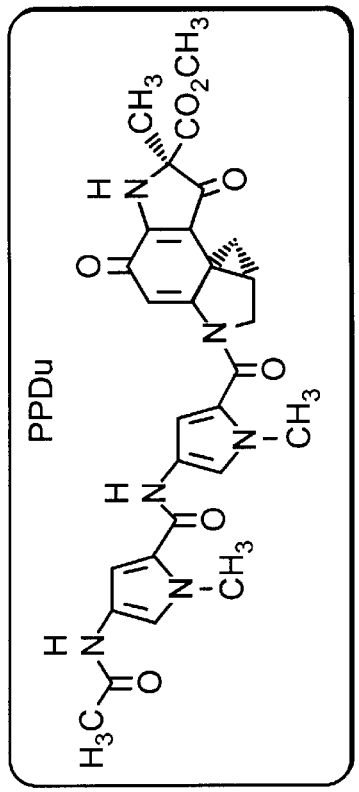
FIG. 3 shows reactivity for the alkylation with PPDu-Dist, wherein a sequence mismatched with PPDu-Dist exerts low reactivity.

FIG. 3 depicts the results of a test using the inventive compound wherein X is CH and R is acetyl group (referred to as PPDu hereinafter) in the same manner as described above.

As described above, PPDu recognizes the nucleotide sequence W-W-v (wherein V represents A or G; and W represents A or T or U). Among 4 oligonucleotides in FIG. 3, PPDu recognizes oligonucleotides with T-T-G (two oligonucleotides on the lower part of FIG. 3) and an oligonucleotide with A-T-G (one oligonucleotide on the upper left of FIG. 3) to efficiently form a covalent bond, while PPDu is mismatched with an oligonucleotide with a nucleotide sequence G-T-G different from the recognition sequences above (on the upper right of FIG. 3) and therefore recognizes the oligonucleotide only slowly at a rate of about 26% even after 22 hours. As has been described above, the inventive compound can thoroughly recognize these sequences.

Figure 4:
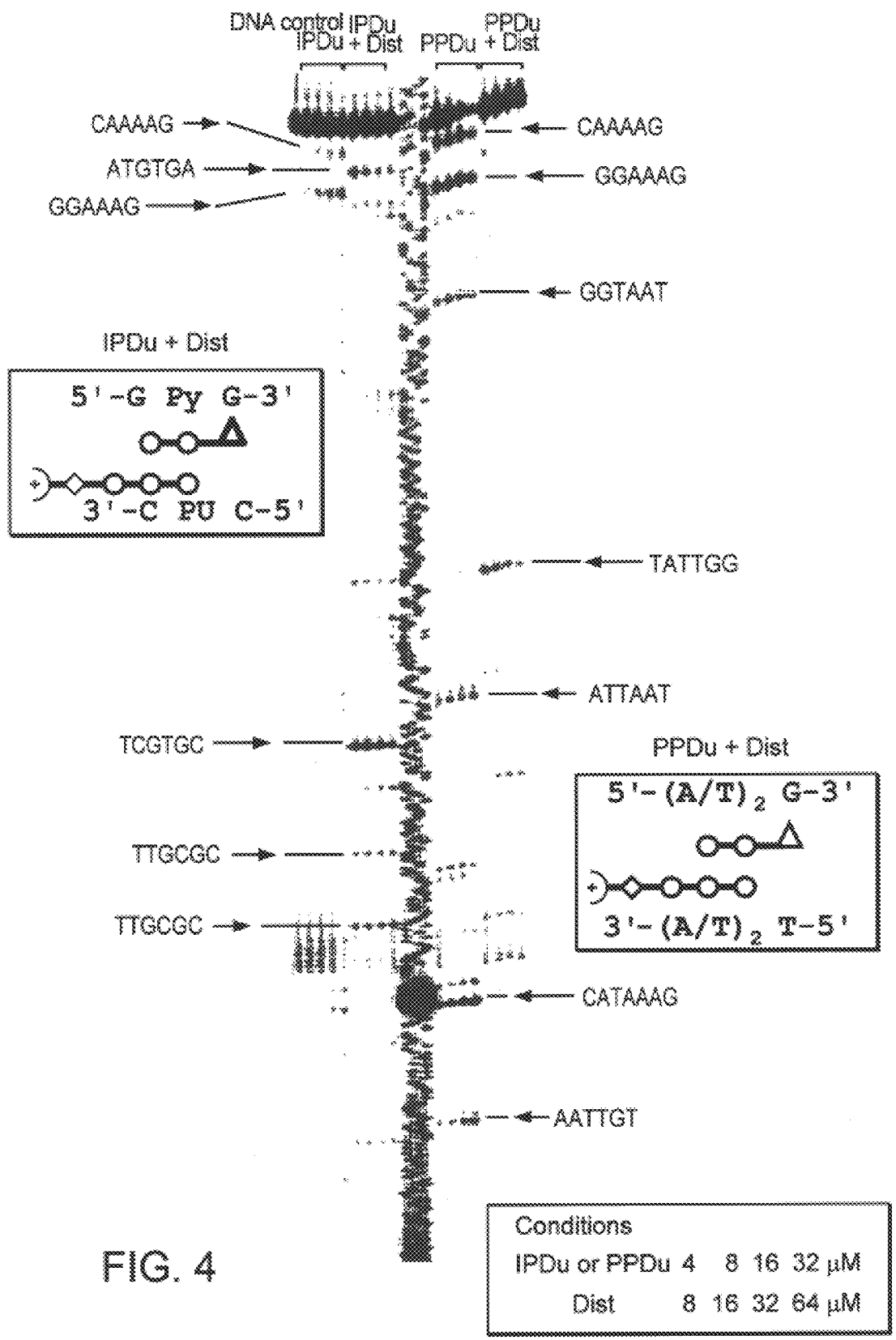
FIG. 4 depicts how IPDu and PPDu recognize a sequence in DNA fragment II'.

FIG. 4 depicts the results of a similar test using a long-chain DNA prepared. The whole nucleotide sequence of the DNA used at the test is shown as SEQ ID NO. 2 in the Sequence Table.

Bonding with PPDu and bonding with IPDu are shown on the right and left, respectively in FIG. 4. It is shown on the right in FIG. 4 that the alkylation with the inventive PPDu occurs at a site with a partial nucleotide sequence W-W-G. It is also shown on the left in FIG. 4 that the alkylation with the inventive PPDu occurs at a site with a partial nucleotide sequence G-W-G.

At the test in FIG. 4, furthermore, IPDu or PPDu was tested at four concentrations, namely 4, 8, 16 and 32 $\mu$M (at each of the concentrations, the concentrations of distamycin (Dist) were 8, 16, 32 and 64 $\mu$M).

Figure 5:
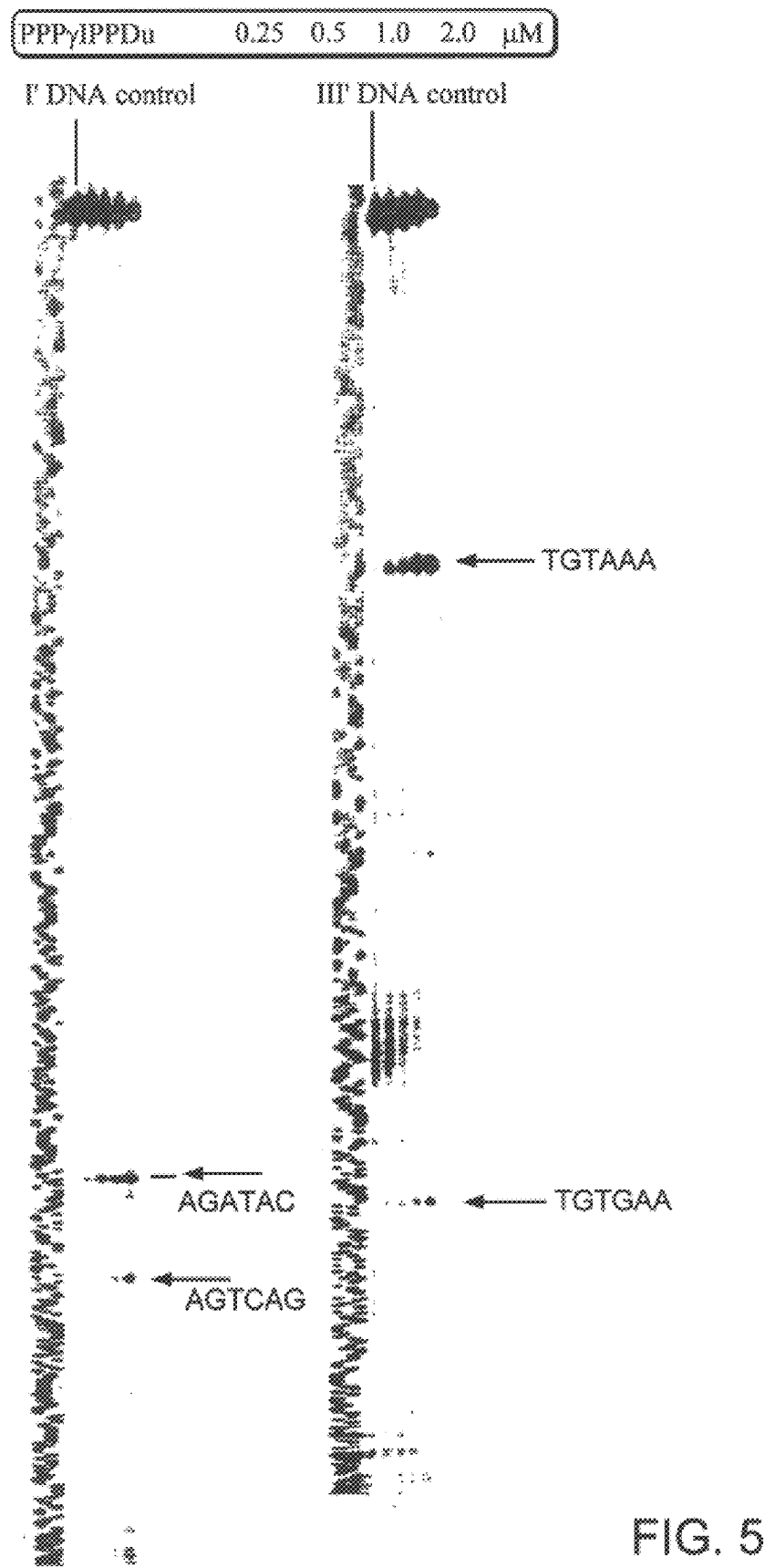
FIG. 5 depicts how IPDu and PPDu recognize a sequence in DNA fragments I' and II'.

FIG. 5 depicts the results of a similar test with Py-Py-Py-γ-Im-Py-Py-Du as the inventive compound and additionally with a 392-bp sequence (I' DNA shown in SQ ID NO. 1 in the Sequence Table) and a 449-bp sequence (III' DNA in SQ ID NO. 3 in the Sequence Table).

Spots due to alkylation are observed at the sites with the partial nucleotide sequence W-W-A as the recognition sequence of PPDu. At the test, the inventive compound was used at four concentrations, namely 0.25, 0.5, 1.0, and 2.0 $\mu$M.

As apparently shown at the tests, the inventive compound can specifically alkylate a specific nucleotide sequence of a gene and thereby inhibit the expression of the gene.

More specifically, the inventive compound can specifically alkylate a target nucleotide sequence part of a gene, thereby inhibiting the function of the gene, to regulate the expression thereof.

FIG. 7 exemplifies preferable compounds in accordance with the invention.

Additionally, the inventive compound is a pyrrole imidazole polyamide, with good cellular permeability. Therefore, the compound can specifically regulate a target gene.

Hence, the invention can provide an alkylating agent specific for a gene, a method for regulating the gene using the same, and a pharmaceutical composition for the therapeutic treatment and prophylaxis of various genetically induced diseases including cancer.

EXAMPLES

The invention will be described more specifically in examples, but is not limited thereto.

Example 1

Production of a Compound wherein X is N and R is Acetyl Group

1. Production of Alkyl Moiety (Du)

Duocarmycin B2 (122 mg; 0.209 mmol) was dissolved in a mixture of methanol (10 ml) and acetonitrile (10 ml) in nitrogen atmosphere, and the resulting mixture was cooled to 0° C. A 28% solution (120 μl) of sodium methoxide in methanol was dropwise added to the mixture. The reaction mixture was agitated at 0° C. for 11 hours, followed by addition of 0.1M phosphate buffer, pH 5.3 (35 ml). After distilling off methanol and adding saline thereto, the resulting residue was extracted in ethyl acetate. The organic layer was dried over sodium sulfate and concentrated. The concentrate was purified by chromatography on a column (chloroform:acetone=1:0 to 3:1), to recover a yellow product (44 mg; a yield of 77%).

$^1$H-NMR(CDCl$_3$)δ; 6.06(s,br,1H), 5.71(s,1H), 5.01(s,br,1H), 3.79(m,1H), 3.71(s,3H), 3.66(d,J=11.0 Hz,1H), 3.01 (m,1H), 2.04(dd,J=3.7 Hz,1H), 1.61(s,3H), 1.00(dd,J=3.7 and 4.9 Hz,1H).

$^{13}$C-NMR(CDCl$_3$)δ; 193.64, 176.55, 174.95, 168.32, 166.84, 108.82, 98.65, 71.14, 53.21, 51.90, 30.49, 24.39, 22.60, 20.98

FABMS m/e 275[M+1]

2. Im-Py Production a. A mixture of 4-amino-N-methyl-imidazol-2-yl-carboxylate ethyl ester hydrochloride salt (3.025 g; 14.7 mmol), pyridine (10 ml) and N, N-diisopropylethylamine (DIEA; 15 ml) was added to acetic anhydride (4 ml) in nitrogen atmosphere. Under agitation at ambient temperature for one hour, the reaction mixture was concentrated to a final volume of about 15 ml. After adding water (100 ml) to the resulting mixture, the mixture was extracted in ethyl acetate. The extract was dried over sodium sulfate and concentrated, which was then cooled to −30° C. to recover an objective N-acetyl derivative (2.64 g; a yield of 85%).

$^1$H-NMR(DMSO-d$_6$) δ; 10.55(s,1H), 7.47(s,1H), 4.25(q, J=7.0 Hz,2H), 3.89(s,3H), 1.97(s,3H), 1.28(t,J=7.0 Hz,3H)

$^{13}$C-NMR(DMSO-d$_6$) δ; 167.00, 158.43, 137.58, 130.77, 114.62, 60.47, 35.32, 22.60, 14.02

HREIMS m/e C$_9$H$_{13}$N$_3$O$_3$ Theoretical value: 211.0957 Experimental value: 211.0960 b. 0.950 g (4.50 mmol) of the N-acetyl derivative recovered above in a. was charged in methanol (16 ml), followed by addition of 2N NaOH (16 ml) thereto. The reaction mixture was agitated at ambient temperature for 3 hours. After distilling off methanol, the remaining aqueous solution was cooled to 4° C. and then adjusted to pH 2, using 1N HCl. The precipitate was collected and rinsed in water and dried, to recover a free carboxylic acid derivative (0.763 g) in white solid (a yield of 93%).

$^1$H-NMR(DMSO-d$_6$) δ; 10.45(s,1H), 7.43(s,1H), 3.87(s, 3H), 1.97(s,3H)

HREIMS m/e C$_7$H$_9$N$_3$O$_3$ Theoretical value: 183.0644 Experimental value: 183.0666 c. A mixture of hydroxybenzotriazole (HOBt; 0.488 g ; 3.61 mmol) and dicyclohexylcarbodiimide (DCC; 0.744 g; 3.61 mmol) was added to a DMF solution (30 ml) of 0.551 g (3.01 mmol) of the free carboxylic acid derivative recovered above in b. The mixture was agitated at ambient temperature for 40 hours, to which was then added a mixture of methyl 4-amino-1-methylpyrrole-2-carboxylate ester hydrochloride salt (0.574 g; 3.01 mmol), DMF (10 ml) and DIEA (15 ml). The mixture was agitated at ambient temperature for 4 days. After filtration and DMF distillation, ethyl acetate (200 ml) was added to the resulting mixture. After removing the precipitate by filtration, the ethyl acetate solution was rinsed in 1N hydrochloric acid, and dried over sodium sulfate and concentrated. The resulting concentrate was cooled to −30° C., to recover an objective amide-methyl ester derivative (0.522 g; a yield of 54%).

$^1$H-NMR(DMSO-d$_6$) δ; 10.19(s,1H), 10.05(s,1H), 7.50(d, J=1.8 Hz,1H), 7.40(s,1H),6.68(d,J=1.8 Hz,1H), 3.93(s,3H), 3.83(s,3H), 3.73(s,3H), 2.01(s,3H)

$^{13}$C-NMR(DMSO-d$_6$) δ; 167.24, 160.73, 155.86, 136.15, 133.78, 121.99, 120.95, 118.78, 114.01, 108.69, 50.93, 36.23, 34.88, 22.69,

HREIMS m/e C$_{14}$H$_{17}$N$_5$O$_4$ Theoretical value: 319.1280 Experimental value: 319.1277 d. The amide-methyl ester derivative (0.500 g) recovered above in c. was dissolved in methanol (12.5 ml), followed by addition of 12.5 ml of 2N NaOH. The solution was agitated overnight at ambient temperature. After distilling off methanol and adding water (20 ml) to the residue, the resulting aqueous solution was subjected to filtration. The resulting aqueous solution was adjusted to pH 2, using 1N hydrochloric acid. The precipitate was collected and dried, to recover an objective free carboxylic acid derivative (0.439 g; a yield of 92%).

$^1$H-NMR(DMSO-d$_6$) δ; 12.18(s,1H), 10.20(s,1H), 9.98(s, 1H), 7.45(s,1H), 7.40(s,1H), 6.92(s,1H), 3.92(s,3H), 3.82(s, 3H), 3.34(s,3H), 2.01(S,3H)

$^{13}$C-NMR (DMSO-d$_6$) δ;

167.23, 161.86, 155.79, 136.15, 133.83, 121.69, 120.42, 119.82, 113.94, 108.74, 36.18, 34.88, 22.69,

HREIMS m/e C$_{13}$H$_{15}$N$_5$O$_4$ Theoretical value: 305.1124 Experimental value: 305.1123 e. The free carboxylic acid derivative (0.135 g; 0.44 mmol) recovered above in d. and 1,1'-carbonyldiimidazole (84 mg) were dissolved in DMF (5 ml). After agitation at ambient temperature for 5 hours, the resulting reaction mixture was poured in cold water (100 ml). The precipitate was collected and rinsed in methylene chloride, dried in vacuo, to recover an objective active amide derivative (0.108 g; a yield of 69%).

$^1$H-NMR(DMSO-d$_6$) δ; 10.18(s,2H), 8.24(s,1H), 7.79(s, 1H), 7.68(S,1H), 7.43(s,1H), 7.13(s,1H), 7.10(d,J=1.9 Hz,1H), 3.94(s,3H), 3.90(s,3H), 2.02(S,3H)

$^{13}$C-NMR(DMSO-d$_6$) δ; 167.28, 156.76, 156.02, 137.76, 136.18, 133.50, 129.75, 124.42, 122.94, 119.90, 118.52, 114.34, 112.13, 36.32, 34.96, 22.70

HREIMS m/e C$_{16}$H$_{17}$N$_7$O$_3$ Theoretical value: 355.1393 Experimental value: 355.1402

3. Amidation

A 60% solution of sodium hydride (7.2 mg; 0.180 mmol) in DMF (0.5 ml) was dropwise added to a DMF solution (0.55 ml) of 19.4 mg (0.071 mmol) of the compound recovered above in 1 at −40° C. in nitrogen atmosphere. After agitation at −40° C. to −20° C. for 2.5 hours, the mixture was cooled to −50° C., followed by addition thereto of a DMF solution (1.0 ml) of the active amide derivative (41.8 mg; 0.118 mmol) recovered above in 2-e. The reaction mixture was agitated at −50° C. to −30° C. for 3 hours. After adding cold 0.1M phosphate buffer, pH 7.0 (20 ml) to the mixture, the resulting solution was extracted in ethyl acetate. The organic layer was dried over sodium sulfate and concentrated. The resulting residue was eluted by TLC with ethyl acetate, to recover the objective IPDU of 15.1 mg (a yield of 34%).

$^1$H-NMR(CDCl$_3$) δ; 8.68(s,1H), 7.68(s,br,1H), 7.33(s, 1H), 7.31(s,1H), 6.51(d,,J=1.81 Hz,1H), 6.43(s,1H), 6.10(s, br,1H), 4.20(dd,,J=5.5 and 4.9 Hz,1H), 4.02(d,J=11.6 Hz,1H), 3.98(s,3H), 3.78(s,3H), 3.67(s,3H), 2.86(m,1H), 2.21(dd,J=3.7 Hz,1H), 2.10(s,3H), 1.59(s,3H), 1.24(t,J=4.3 Hz,1H)

HRFABMS m/e 562.2054 [M+H] (Theoretical value of C$_{27}$H$_{28}$N$_7$O$_7$: 562.2050)

Example 2

Production of Compound wherein X is CH and R is Acetyl Group

1. Py-Py Production a. In the same manner as in Example 1-2-a., a pyrrole derivative was recovered (a yield of 91%).

$^1$H-NMR(CDCl$_3$) δ; 7.79(s,1H),7.26(d,J=1.8 Hz,1H), 6.60(d,J=1.8 Hz,1H), 3.78(s,3H), 3.72(s,3H), 2.05(s,3H)

$^{13}$C-NMR(DMSO-d$_6$) δ; 166.52, 160.70, 122.81, 120.28, 118.56, 107.58, 50.87, 36.06, 22.95

HREIMS m/e C$_9$H$_{12}$N$_2$O$_3$ Theoretical value: 196.0848 Experimental value: 196.6837 b. In the same manner as in Example 1-2-b., a pyrrole derivative was recovered (a yield of 84%).

$^1$H-NMR(DMSO-d$_6$) δ; 9.80(s,1H),7.24(d,J=1.8 Hz,1H), 6.62(d,J=1.8 Hz,1H), 3.77(s,3H), 1.93(s,3H)

$^{13}$C-NMR(DMSO-d$_6$) δ; 166.49, 161.83, 122.53, 119.83, 119.57, 107.61, 36.06, 22.95

HREIMS m/e C$_8$H$_{10}$N$_2$O$_3$ Theoretical value: 182.0691 Experimental value: 182.0682 c. In the same manner as in Example 1-2-c., a pyrrole derivative was recovered (a yield of 51%).

$^1$H-NMR(DMSO-d$_6$) δ; 9.87(s,1H), 9.80(s,1H), 7.43(d, J=2.0 Hz,1H), 7.12(d,J=2.0 Hz,1H),6.88(d,J=2.0 Hz,1H), 6.82(d,J=2.0 Hz,1H),3.82(s,3H),3.80(s,3H), 3.72(s,3H), 1.95(s,3H)

$^{13}$C-NMR(DMSO-d$_6$) δ; 166.42, 160.74, 158.36, 122.84, 122.45, 122.13, 120.70, 118.48, 118.12, 108.36, 103.84, 50.87, 36.08, 36.00, 22.98

HREIMS m/e C$_{15}$H$_{18}$N$_4$O$_4$ Theoretical value: 318.1328 Experimental value: 318.1310 d. In the same manner as in Example 1-2-d., a pyrrole derivative was recovered (a yield of 87%).

$^1$H-NMR(DMSO-d$_6$) δ; 9.83(s,1H), 9.79(s,1H), 7.39(d,J= 2.0 Hz,1H), 7.12(d,J=2.0 Hz,1H), 6.82(dd,J=2.0 and 1.5 Hz,2H), 3.80(s,6H), 1.96(s,3H)

$^{13}$C-NMR(DMSO-d$_6$) δ; 166.42, 161.88, 158.33, 122.53 (d), 122.12, 120.24, 119.47, 118.05, 108.36, 103.82, 36.04, 35.98, 23.00

HREIMS m/e C$_{14}$H$_{16}$N$_5$O$_4$ Theoretical value: 304.1171 Experimental value: 304.1167 e. In the same manner as in Example 1-2-e., a pyrrole derivative was recovered (a yield of 74%).

$^1$H-NMR(DMSO-d$_6$) δ; 9.98(s,1H),9.80(s,1H),8.25(s, 1H), 7.75(d,J=1.5 Hz,1H),7.68(t,J=2.0 and 1.0 Hz,1H), 7.13 (t,J=2.0 and 1.0 Hz,2H), 6.93(d,J=1.5 Hz,1H), 6.88(d,J=1.5 Hz,1H),3.90(s,3H),3.82(s,3H), 1.96(s,3H)

$^{13}$C-NMR (DMSO-d$_6$) δ; 166.47, 158.46, 156.75, 137.70, 129.67, 124.32, 123.88, 122.25 122.13, 119.68, 118.56, 118.40, 111.69, 104.04, 36.23, 36.10, 23.02

HREIMS m/e C$_{17}$H$_{18}$N$_6$O$_3$ Theoretical value: 354.1440 Experimental value: 354.1442

2. Amidation

In the same manner as in Example 1-3, a pyrrole derivative PPDu was recovered (a yield of 26%).

$^1$H-NMR(CDCl$_3$) δ; 8.28(s,br,1H),7.78(s,br,1H),7.32(s, 1H),6.94(s,1H), 6.64(s,1H), 6.55(s,1H), 6.43(s,1H), 6.39(s, 1H), 4.20(dd,J=5.5 and 4.9 Hz,1H), 4.00(d,J=12.0 Hz,1H), 3.81(s,3H),3.76(s,3H),3.70(s,3H), 2.90–2.86(m,1H), 2.21 (dd,J=3.7 Hz,1H), 2.03(s,3H), 1.23(s,3H), 0.86(t,J=4.3 Hz,1H)

HRFABMS m/e 561.2089 [M+H] (Theoretical value of C$_{28}$H$_{29}$N$_6$O$_7$: 561.2098)

Example 3

Alkylation Test

A 8-mer DNA was synthetically produced, using a DNA automatic synthesizer. Alkylation of the oligonucleotide DNA was conducted as follows. The inventive compound (0.1 mM), distamycin A (0.1 mmol) and the 8-mer DNA (1 mM) were added to 50 mM sodium carbonate buffer, pH 7.0. The resulting mixture was incubated at 0° C. for different periods of time. The reaction was monitored by HPLC (on a Chemcobond 5-ODS-H column). The eluent was a linear gradient of 0.05 M ammonium formate and 0 to 50% acetonitrile (0 to 40 minutes), at a flow of 1.0 ml/min. Detection was conducted at 254 nm.

The results with the inventive IPDu are shown in FIG. 2.

The results with the inventive PPDu are shown in FIG. 3.

Example 4

Alkylation Test of Long-chain DNA with IPDu and PPDu

A 5'-Texas Red-end-modified 450-bp DNA was prepared by PCR. The sequence 378–395 of 5'-Texas Red-end-modified pUC18 and the sequence 1861–1881 of inverted pUC18 were used.

In the same manner as in Example 3, an alkylation test was conducted.

The results are shown in FIGS. 4 and 5.

ADVANTAGES OF THE INVENTION

The invention provides a compound capable of specifically alkylating a specific nucleotide sequence. The inventive compound can alkylate a target nucleotide sequence in a DNA, selectively and specifically, whereby the expression of the DNA with the nucleotide sequence can be regulated. Thus, the inventive compound is useful for therapeutic treatment and prophylaxis of various DNA-induced diseases.

What is claimed is:

1. A compound according to formula I:

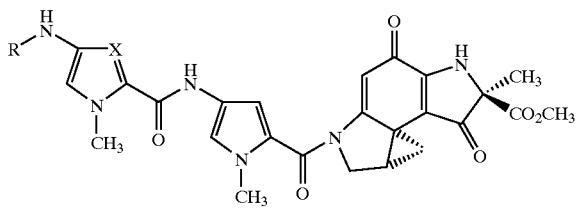

wherein

R represents a lower amyl group or a polyamide group; and X represents nitrogen or CH.

2. A compound according to claim 1, wherein R is methyl group.

3. A compound according to claim 1, wherein R is a polyamide group with an N-methylpyrrole ring and/or an N-methylimidazole ring.

4. A compound according to claim 3, wherein R contains a γ-linker represented by a group —CO—(CH$_2$)$_3$—NH—.

5. An alkylating agent of genes, the agent comprising a compound according to any one of claims 1 to 4.

6. An alkylating agent according to claim 5, wherein the nucleotide sequence recognized for alkylation is either the sequence W-W-V wherein V represents A or G and W represents A or T or U or the sequence G-W-V wherein V represents A or G and W represents A or T or U.

7. An alkylating agent according to claim 5, characterized in that the agent is used in combination with distamycin.

8. An alkylating agent according to claim 6, characterized in that the agent is used in combination with distamycin.

9. A composition with a pharmaceutically acceptable carrier for prophylaxis of a gene-inducible disease, the composition containing a compound according to any one of claims 1 to 4.

* * * * *